(12) United States Patent
Takatori et al.

(10) Patent No.: US 9,486,598 B2
(45) Date of Patent: Nov. 8, 2016

(54) OXYGEN MASK

(75) Inventors: Fumihiko Takatori, Tokyo (JP); Shinji Yamamori, Tokyo (JP); Masayuki Inoue, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 123 days.

(21) Appl. No.: 12/912,035

(22) Filed: Oct. 26, 2010

(65) Prior Publication Data

US 2011/0094513 A1    Apr. 28, 2011

(30) Foreign Application Priority Data

Oct. 28, 2009  (JP) ................................ 2009-247695
Apr. 9, 2010  (JP) ................................ 2010-090629

(51) Int. Cl.
  *A62B 18/02*  (2006.01)
  *A61M 16/06*  (2006.01)
  *A61M 16/08*  (2006.01)

(52) U.S. Cl.
  CPC ........... *A61M 16/06* (2013.01); *A61M 16/085* (2014.02); *A61M 16/0816* (2013.01); *A61M 2202/0208* (2013.01); *A61M 2206/14* (2013.01); *A61M 2230/432* (2013.01)

(58) Field of Classification Search
  CPC .................................................. A61M 16/06
  USPC ........... 128/205.25, 206.21, 206.28, 207.12, 128/207.13
  See application file for complete search history.

(56) References Cited

U.S. PATENT DOCUMENTS

| | | | |
|---|---|---|---|
| 2,313,999 A | 3/1943 | Kreiselman | |
| 2,675,803 A | 4/1954 | Kaslow | |
| 3,682,171 A * | 8/1972 | Dali et al. | 128/207.18 |
| 3,889,671 A * | 6/1975 | Baker | 128/207.13 |
| 4,201,205 A | 5/1980 | Bartholomew | |
| 4,216,769 A * | 8/1980 | Grimes | 128/207.13 |
| 4,258,710 A * | 3/1981 | Reber | 128/204.18 |
| 4,266,540 A | 5/1981 | Panzik et al. | |
| 4,454,880 A | 6/1984 | Muto et al. | |
| 6,561,190 B1 | 5/2003 | Kwok | |
| 6,595,207 B1 | 7/2003 | McDonald et al. | |
| 2001/0042547 A1 | 11/2001 | McDonald et al. | |
| 2003/0168063 A1* | 9/2003 | Gambone et al. | 128/203.16 |
| 2005/0257794 A1 | 11/2005 | Aylsworth et al. | |
| 2006/0196510 A1* | 9/2006 | McDonald et al. | 128/206.21 |
| 2007/0175473 A1 | 8/2007 | Lewis et al. | |

(Continued)

FOREIGN PATENT DOCUMENTS

EP    0 053 449 A1   6/1982
JP    2-94566 U      7/1990

(Continued)

OTHER PUBLICATIONS

Partial European Search Report Feb. 24, 2011.

(Continued)

*Primary Examiner* — Kristen Matter
(74) *Attorney, Agent, or Firm* — Kenealy Vaidya LLP

(57) ABSTRACT

An oxygen mask can include an oxygen supply unit and an attachment unit which is to be attached to a periphery of a nose or a nose and a mouth of a patient. The attachment unit includes an opening which communicates with external air and which is formed at a position to which, when the oxygen mask is attached to the patient, at least one of the nose and the mouth of the patient is opposed.

23 Claims, 10 Drawing Sheets

(56) References Cited

U.S. PATENT DOCUMENTS

| | | |
|---|---|---|
| 2008/0060649 A1 | 3/2008 | Veliss et al. |
| 2008/0196715 A1* | 8/2008 | Yamamori ............... 128/203.12 |
| 2008/0319334 A1 | 12/2008 | Yamamori |
| 2011/0041855 A1* | 2/2011 | Gunaratnam et al. ... 128/207.18 |
| 2011/0319783 A1 | 12/2011 | Lindholt et al. |

FOREIGN PATENT DOCUMENTS

| | | |
|---|---|---|
| JP | 2000-14785 A | 1/2000 |
| JP | 2001-511035 A | 8/2001 |
| JP | 2003-533296 A | 11/2003 |
| JP | 2004-507333 A | 11/2003 |
| JP | 2005-253925 A | 3/2004 |
| JP | 3102973 U | 7/2004 |
| JP | 2005-304574 A | 11/2005 |
| JP | 2008-500132 A | 1/2008 |
| JP | 2006-68471 A | 9/2008 |
| JP | 2009-519759 A | 5/2009 |
| WO | 98/29153 A1 | 7/1998 |
| WO | 01/87394 A2 | 11/2001 |
| WO | 2006/039788 A1 | 4/2006 |
| WO | 2007/128100 A1 | 11/2007 |
| WO | 2008/011682 A1 | 1/2008 |
| WO | 2009/003488 A2 | 1/2009 |
| WO | 2009/108995 A1 | 9/2009 |

OTHER PUBLICATIONS

European Search Report Jul. 4, 2011.
Japanese Office Action for the related Japanese Patent Application No. 2010-090629 dated Jan. 15, 2014.
Chinese Office Action for the related Chinese Patent Application No. 201010529515.2 dated Mar. 4, 2014.
Japanese Office Action for the related Japanese Patent Application No. 2010-090629 dated Jul. 10, 2013.
Japanese Office Action for the related Japanese Patent Application No. 2014-069555 dated Apr. 7, 2015.
Chinese Office Action for the related Chinese Patent Application No. 201010529515.2 dated Nov. 3, 2014.
Chinese Office Action for the related Chinese Patent Application No. 201410344424.X dated Aug. 17, 2016.

* cited by examiner

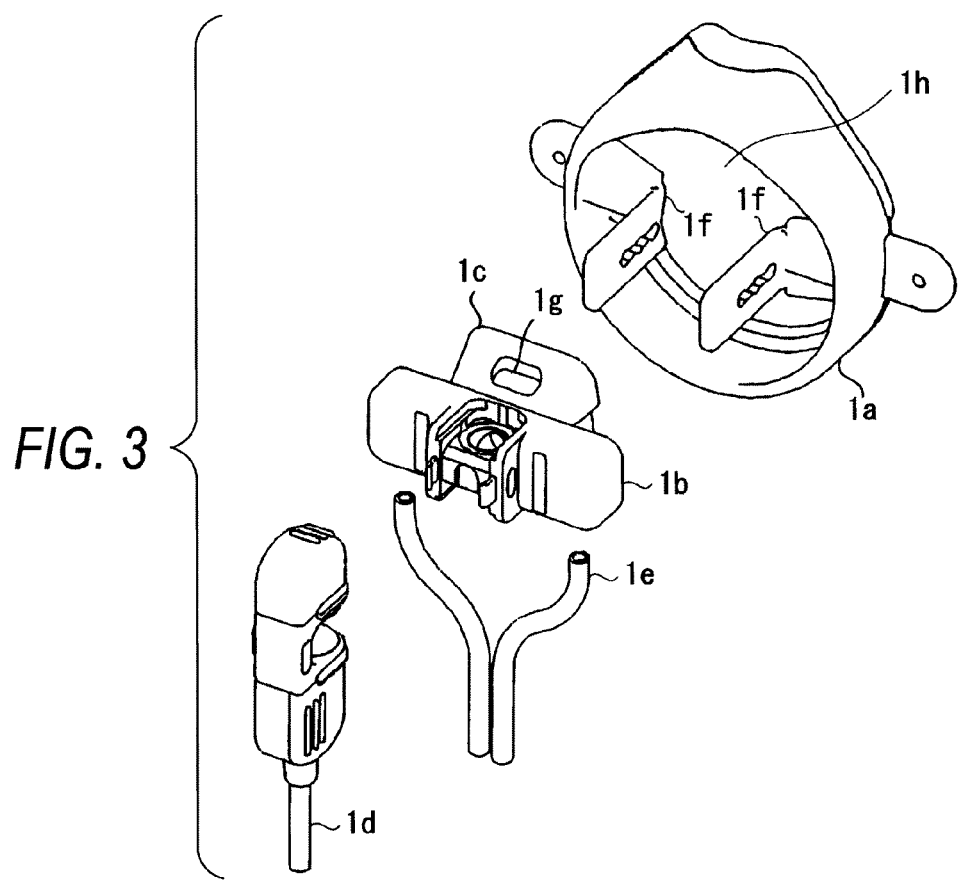

OXYGEN MASK

BACKGROUND OF THE INVENTION

The present invention relates to an oxygen mask which is attached to the patient to supply oxygen thereto, and more particularly to an oxygen mask to and from which an expired gas concentration measurement sensor is attachable and detachable.

An oxygen diffuser which supplies oxygen to the patient is disclosed in JP-T-2004-507333. The oxygen diffuser disclosed in JP-T-2004-507333 is described as follows with reference to FIG. 8.

The diffuser 20 shown in section in FIG. 8 has a body 31 formed from a wall 32, of somewhat triangular, cup-shaped appearance which follows the shape of the nose/mouth nexus of a patient. This wall extends from a base 33 where an oxygen outlet 34 is positioned, outwardly and upwardly to an edge 35 of triangular peripheral shape. As it approaches this edge 35, wall 32 becomes more "vertical" (with opposite sides being parallel) than outwardly extending. This shaping of the body wall permits a concentration of the oxygen and a shaping of the plume of oxygen-enriched, thus providing a more precise direction of this plume towards the patient's nose/mouth contour. The peripheral corners are rounded, with one of the corners 36, intended to be the uppermost corner when in use, and the proximal portions of the wall edge, are raised with respect to the other corners and edge portions as illustrated, also to facilitate the direction of oxygen towards a patient's nose and mouth. This construction, with protruding corner 36 and proximal edges of the wall, being positioned proximal to the patient's nose when in use, and the wider triangular portion at the bottom proximal a patient's mouth, provides optimal oxygen delivery to a patient.

A mushroom-shaped baffle 40, having a central post 42 which is seated in and over the oxygen outlet 34, is provided to assist in the diffusion of oxygen and avoid a direct flow of oxygen towards the patient's face. The upper end of baffle 40 has a curled-back lip 42 of conical shape so that oxygen flowing from the oxygen outlet 34 is directed into and against the underside 44 of this lip, creating turbulence and mixing the pure oxygen with the ambient air.

In other words, baffle 40 impedes oxygen flow directly from base 33, changing the oxygen transmission flow from a jet to a turbulent, plume-like flow.

Centrally located with post 42, extending from its bottom and through upper end 44, is a passageway 48 to permit gas analysis of expired gases from the patient. The passageway 48 provides a fluid communication from the environment in front of the patient's mouth and nose (when the delivery system is in operation) to the oxygen/carbon dioxide inlet port 28.

As a further configuration for supplying oxygen to the patient, JP-A-2006-68471 discloses an art in which tubes are inserted into the nostrils of the patient to supply oxygen thereto.

As a further configuration for supplying oxygen to the patient, JP-A-2005-253925 discloses an art in which oxygen is supplied to the patient through a mask which covers the nostrils and mouth of the patient.

As shown in FIG. 8, the diffuser 20 disclosed in JP-T-2004-507333 is configured by the wall 32 of somewhat triangular, cup-shaped appearance which follows the shape of the nose/mouth nexus of the patient. Therefore, the supply of oxygen and the concentration measurement of the expired gas can be simultaneously performed. However, the diffuser causes oxygen to directly flow into the nose and the mouth, and hence there is a problem in that the expired gas is diluted by oxygen and the concentration of the expired gas cannot be correctly measured. Particularly, it is very difficult to perform the measurement on mouth respiration.

Particularly, the expired gas concentration measurement used in JP-T-2004-507333 is performed by the side stream system in which the expired gas must be sucked through a sampling tube such as a tube 24. Therefore, also supplied oxygen is sucked, and there is a possibility that the expired gas is diluted.

In the oxygen supply which is performed through the tube, and which is disclosed in JP-A-2006-68471, there is a problem in that oxygenation is not performed in the case of mouth respiration. When a large amount of oxygen is supplied in order to enhance the efficiency of oxygenation, the nostrils are dried. Therefore, oxygen of a predetermined amount or more cannot be supplied.

In the oxygen supply which is performed through the mask, and which is disclosed in JP-A-2005-253925, there is a problem in that the interior of the mask is airtight and hence high concentration $CO_2$ which has been expired is again inspired. In order to prevent such rebreathing from occurring, oxygen must be supplied at a rate of 5 L per minute or more. Therefore, there are problems such as that oxygen is wastefully used, and that, during attachment of the mask, the eyes are dried.

SUMMARY

It is therefore an object of the invention to provide an oxygen mask in which efficient oxygenation is realized by a small supply amount of oxygen, rebreathing is reduced, and the degree at which the expired gas is diluted by oxygen is reduced, thereby enabling the concentration of the expired gas to be correctly measured.

In order to achieve the object, according to the invention, there is provided an oxygen mask, which comprises an oxygen supply unit 1b' and an attachment unit 1a' which is to be attached to a periphery of a nose or a nose and a mouth of a patient, the oxygen mask wherein the attachment unit includes an opening which communicates with external air and which is formed at a position to which, when the oxygen mask is attached to the patient, at least one of the nose and the mouth of the patient is opposed.

In order to achieve the object, according to the invention, there is also provided an oxygen mask, which comprises an oxygen supply unit and an attachment unit which is to be attached to a periphery of a nose or a nose and a mouth of a patient, the oxygen mask wherein the attachment unit includes: an opening which communicates with external air; and an oxygen scattering plate which is opposed to an oxygen blow out port of the oxygen supply unit.

The oxygen scattering plate may be formed by a bridging member between an attachment portion of the attachment unit and the oxygen supply unit.

The oxygen scattering plate may have a bent shape.

The oxygen mask may further include: an expired gas introduction unit into which expired gas in the oxygen mask is introduced; and an expired gas concentration measurement unit being attachable to and detachable from an outer side of the expired gas introduction unit.

The oxygen mask may further include: an expired gas introduction unit into which expired gas in the oxygen mask is introduced; and a sampling tube is attachable to and detachable from an outer side of the expired gas introduction unit.

The expired gas concentration measurement unit may be movably attached to the expired gas introduction unit.

The sampling tube may be movably attached to the expired gas introduction unit.

The oxygen mask may further include an adjusting unit which adjusts an attaching position of the expired gas introduction unit.

The expired gas introduction unit may include a rebreathing prevention hole for preventing rebreathing of expired gas from occurring.

A portion of the oxygen mask which is to be in contact with the patient may be inwardly curled.

An insertion port of a stomach tube may be formed in a portion of the oxygen mask which is to be in contact with the patient.

An oxygen supplying tube is connected to the oxygen supply unit from a side face of the oxygen mask.

In order to achieve the object, according to the invention, there is also provided an oxygen mask, which comprises an oxygen supply unit and an attachment unit which is to be attached to a periphery of a nose or a nose and a mouth of a patient, the oxygen mask wherein an oxygen supplying tube is connected to the oxygen supply unit from a side face of the oxygen mask, and the attachment unit includes an opening which communicates with external air.

The oxygen mask may further include: an expired gas introduction unit into which expired gas in the oxygen mask is introduced; and an expired gas concentration measurement unit being attachable to and detachable from an outer side of the expired gas introduction unit.

The oxygen mask may further include: an expired gas introduction unit into which expired gas in the oxygen mask is introduced; and a sampling tube is attachable to and detachable from an outer side of the expired gas introduction unit.

The expired gas introduction unit may include a rebreathing prevention hole for preventing rebreathing of expired gas from occurring.

A portion of the oxygen mask which is to be in contact with the patient may be inwardly curled.

BRIEF DESCRIPTION OF THE DRAWINGS

FIG. 3 is a perspective view of the oxygen mask of the invention which is disassembled into components.

DETAILED DESCRIPTION OF EMBODIMENTS

FIGS. 1A to 1D are views showing an example of the configuration of the oxygen mask of the invention in a state where an expired gas concentration measurement unit is attached to the mask.

Figure 1A:
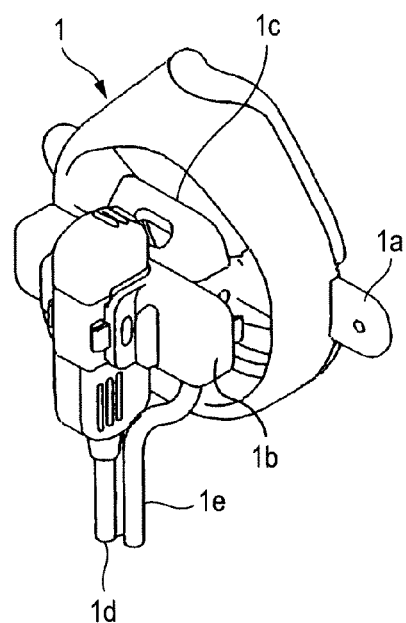
FIGS. 1A to 1D are views showing an example of the configuration of the oxygen mask of the invention in a state where an expired gas concentration measurement unit is attached to the mask.

FIG. 1A is a perspective view of an oxygen mask 1 in a state where an expired gas concentration measurement unit is attached to a mask, 1a denotes the mask, 1b denotes an oxygen blow out unit, 1c denotes an expired gas introduction unit, 1d denotes the expired gas concentration measurement unit, and 1e denotes an oxygen tube.

Figure 1B:
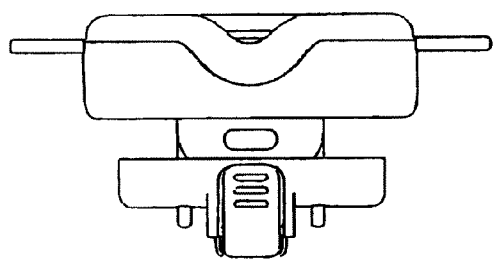
Figure 1C:
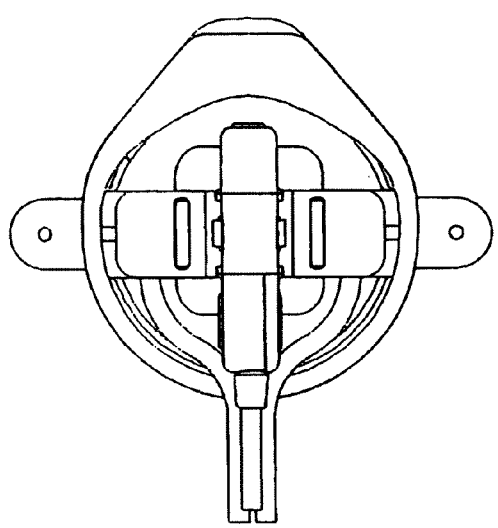
Figure 1D:
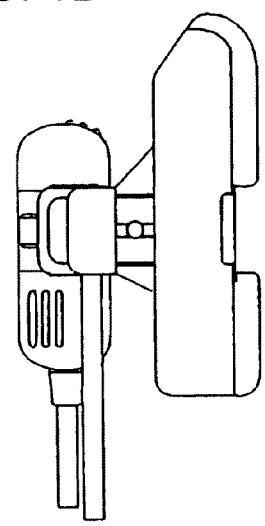

FIG. 1B is a top view of FIG. 1A, FIG. 1C is a front view, and FIG. 1D is a side view.

FIGS. 2A to 2D are views showing an example of the configuration of the oxygen mask 1 shown in FIGS. 1A to 1D in a state where the expired gas concentration measurement unit 1d is detached from the mask 1a.

Figure 2A:
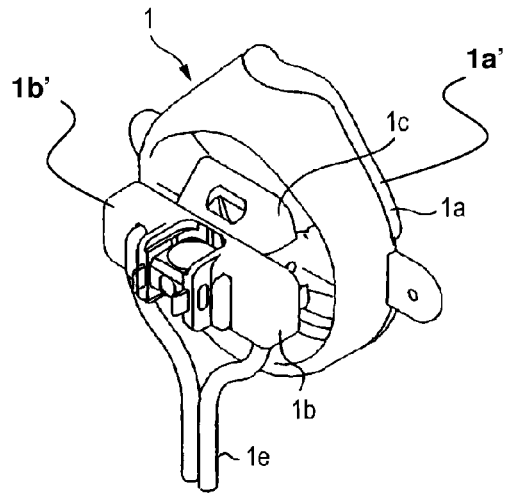
FIGS. 2A to 2D are views showing the configuration of the oxygen mask of FIGS. 1A to 1D in a state where the expired gas concentration measurement unit is detached from the mask.

FIG. 2A is a perspective view of the oxygen mask 1 in a state where the expired gas concentration measurement unit 1d is detached from the mask 1a.

Figure 2B:
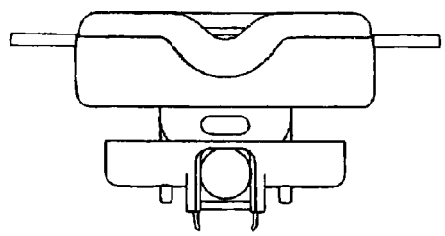
Figure 2C:
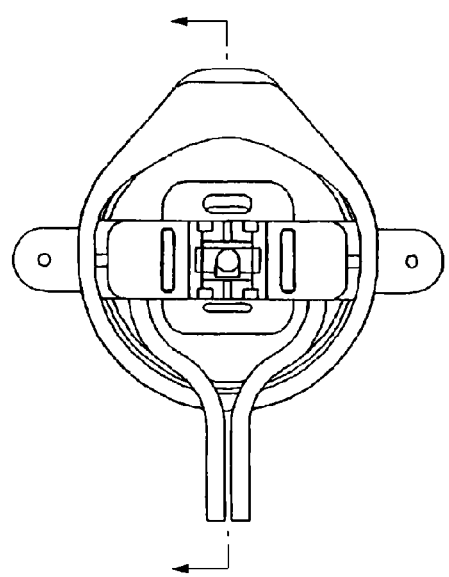
Figure 2D:
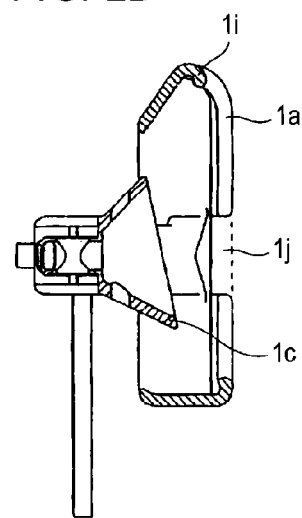

FIG. 2B is a top view of FIG. 2A, FIG. 2C is a front view of FIG. 2A, and FIG. 2D is a section view taken along arrow portions in FIG. 2C.

As shown in FIG. 2D, the expired gas introduction unit 1c in the invention is configured so as to be adjustable with respect to the mask 1a in order to optimize the introduction of the expired gas.

As described above, the attachment to the outer side (opposite to the face to the patient) of the expired gas introduction unit 1c to which the expired gas in the mask 1a is introduced may be structured in any manner as far as the expired gas concentration measurement unit 1d is attachable to and detachable from the outer side.

Although the embodiment will be illustrated by using a main stream type sensor which directly measures the expired gas, as the expired gas concentration measurement unit 1d, the invention is not limited to this. Alternatively, a side stream type sensor in which the expired gas is sucked through a sampling tube (not shown) may be used as the expired gas concentration measurement unit 1d. In the alternative, a structure where the sampling tube can be detached from the outer side (opposite to the face to the patient) of the expired gas introduction unit 1c may be formed.

Preferably, the attachment of the expired gas concentration measurement unit 1d to the expired gas introduction unit 1c is movable. Specifically, as shown in FIG. 10C, the attached expired gas concentration measurement unit 1d may be movable in the clockwise/counterclockwise direction Y, or in the anteroposterior direction so that the expired gas concentration measurement unit 1d approaches or separates from the subject. The expired gas concentration measurement unit 1d is requested to be movable so that, in the state where the expired gas concentration measurement unit 1*d* is attached to the mask 1*a*, the unit does not hinder procedures such as an oral care on the subject.

Figure 10B:
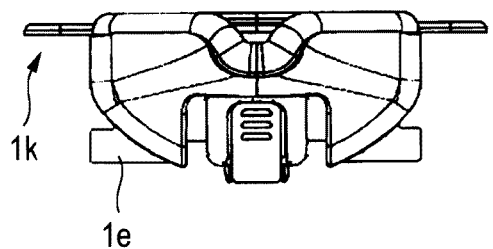
FIGS. 10A to 10D are views showing another example of the configuration of the oxygen mask of the invention in a state where an expired gas concentration measurement unit is attached to the mask.
Figure 10A:
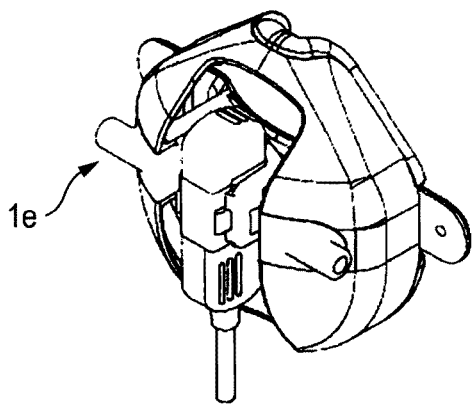
Figure 10C:
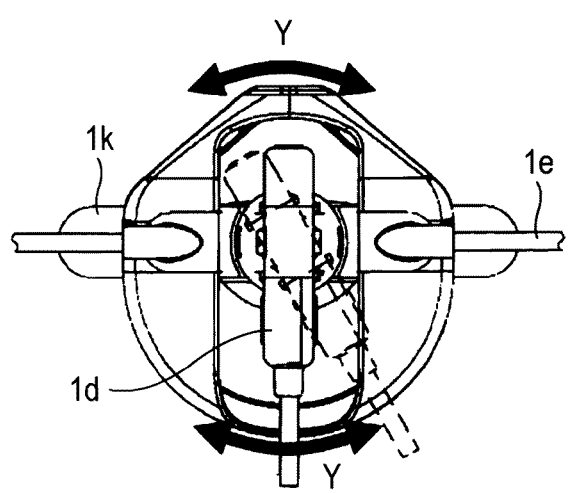
Figure 10D:
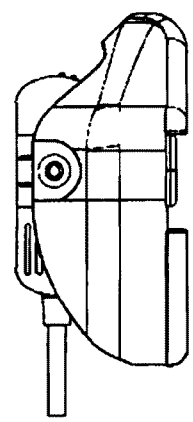

Referring to FIGS. 1A to 2D, the oxygen tube 1*e* is connected from the lower side of the mask 1*a*, and, when the mask 1*a* is attached to the subject, fixed by a string or rubber band which is passed through a fixing member 1*k* shown in FIG. 10A.

As shown in FIGS. 10A to 10D, the oxygen tube 1*e* may be connected from the lateral side of the mask 1*a*. In this case, the oxygen tube 1*e* extends from an ear of the subject toward the nostrils or the oral cavity, and hence the mask 1*a* can be fixed to the subject by winding the oxygen tube 1*e* around the ear or the like of the subject. In this case, the fixing member 1*k* may be removed. Since a member such as the fixing member 1*k* is not necessary, the number of components can be reduced, and the shape of the oxygen mask 1 is simplified, so that the oxygen mask 1 can be easily produced.

FIG. 3 is a perspective view of the oxygen mask 1 of the invention which is disassembled into components.

Oxygen scattering plates 1*f* attached to the mask of FIG. 3 are placed while being opposed to an oxygen blow out port of the oxygen blow out unit 1*b*, to scatter the blown out oxygen, thereby preventing the oxygen from being directly blown to the face of the patient wearing the oxygen mask 1. The presence of the oxygen scattering plates 1*f* causes the oxygen concentration to be uniformalized, and, even when a large amount of oxygen is supplied, inhibits the oxygen from being directly hit to the skin, whereby the skin is prevented from being dried.

A rebreathing prevention hole 1*g* which reduces rebreathing of CO2 is formed in the expired gas introduction unit 1*c* of FIG. 3.

Figure 9:
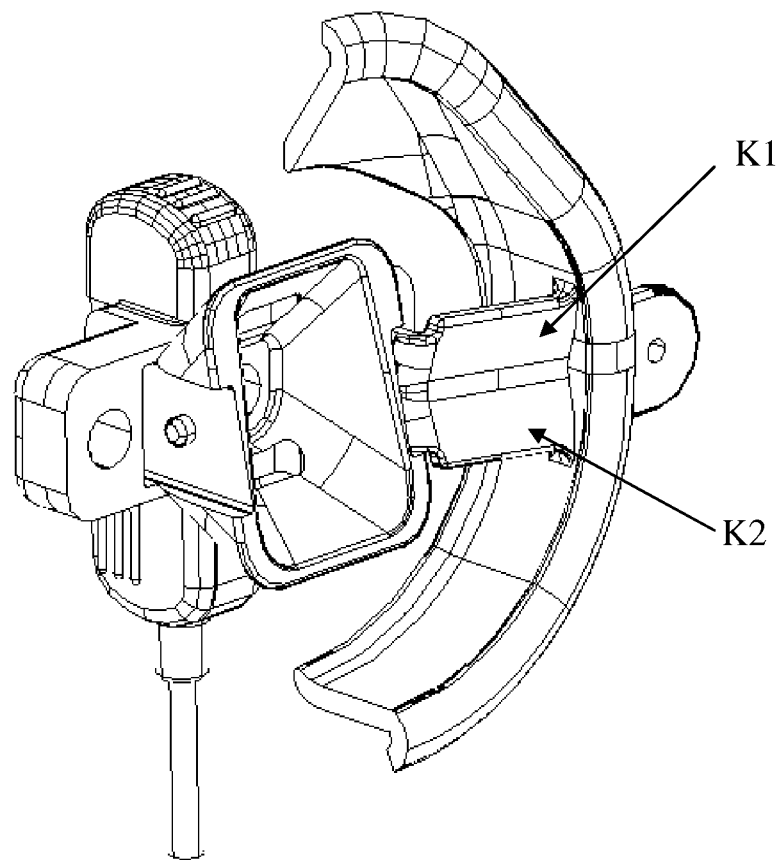
FIG. 9 is an enlarged view of oxygen scattering plates and expired gas introduction unit of the oxygen mask of the invention.

The oxygen scattering plates 1*f* may have a shape in which the oxygen scattering plates are bent as indicated by K1 and K2 in FIG. 9. In the case of the shape shown in FIG. 9, oxygen which collides with the side of K1 of each oxygen scattering plate is efficiently guided toward the nostrils, and that which collides with the side of K2 of each oxygen scattering plate is guided toward the oral cavity.

In the mask 1*a* of FIG. 3, as shown in the figure, a large opening 1*h* is formed in a portion opposed to a portion which is to be attached to the face of the patient, and hence it is possible to prevent a situation where the interior of the mask 1*a* is filled with the expired gas due to respiration of the patient and becomes stuffy, from occurring. Preferably, the opening 1*h* is opened in the mask face which, when the mask is attached to the patient, is opposed to the face of the patient. The opening 1*h* is effective in rebreathing, and facilitates procedures by a medical person such as visual inspection and an oral care.

As shown in the section view of FIG. 2D, an inward curl 1*i* is formed in a portion of the mask which is to be attached to the face of the patient. Therefore, oxygen is prevented from escaping through the attaching portion with respect to the patient, and the oxygen concentration in the mask is maintained high.

As shown by 1*j* in FIG. 2, a passing hole for a stomach tube is formed in the portion of the mask which is to be attached to the face of the patient, it is possible to prevent oxygen from escaping through the attaching portion with respect to the patient.

Figure 4:
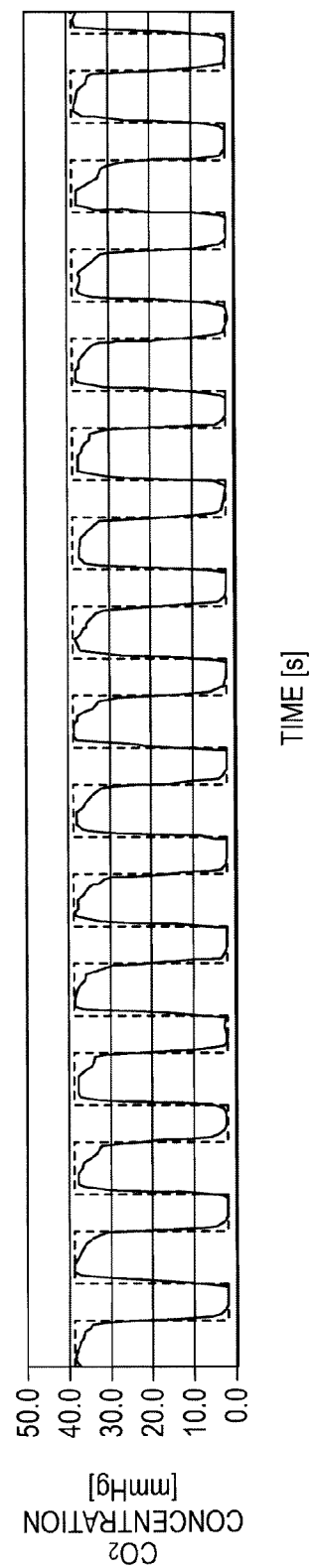
FIG. 4 is a view showing results of measurements of the CO2 concentration due to respiration in the case where the patient wears the oxygen mask of the invention.

Next, FIG. 4 shows results of measurements of the CO2 concentration due to respiration in the case where the patient wears the oxygen mask of the invention.

In FIG. 4, the ordinate shows the CO2 concentration, the unit of the ordinate is mmHg, and the abscissa shows the time and indicates the CO2 concentration of each respiration of the patient.

In FIG. 4, the rectangular wave indicated by the broken line shows an ideal waveform of the CO2 concentration which changes between substantially zero and 40 mmHg, and the solid line shows the CO2 concentration which is measured by the oxygen mask of the invention. It is seen that the measured concentration substantially coincides with the ideal waveform.

Next, the effect of the countermeasure for reducing rebreathing in the oxygen mask of the invention will be described with reference to FIG. 5.

Figure 5:
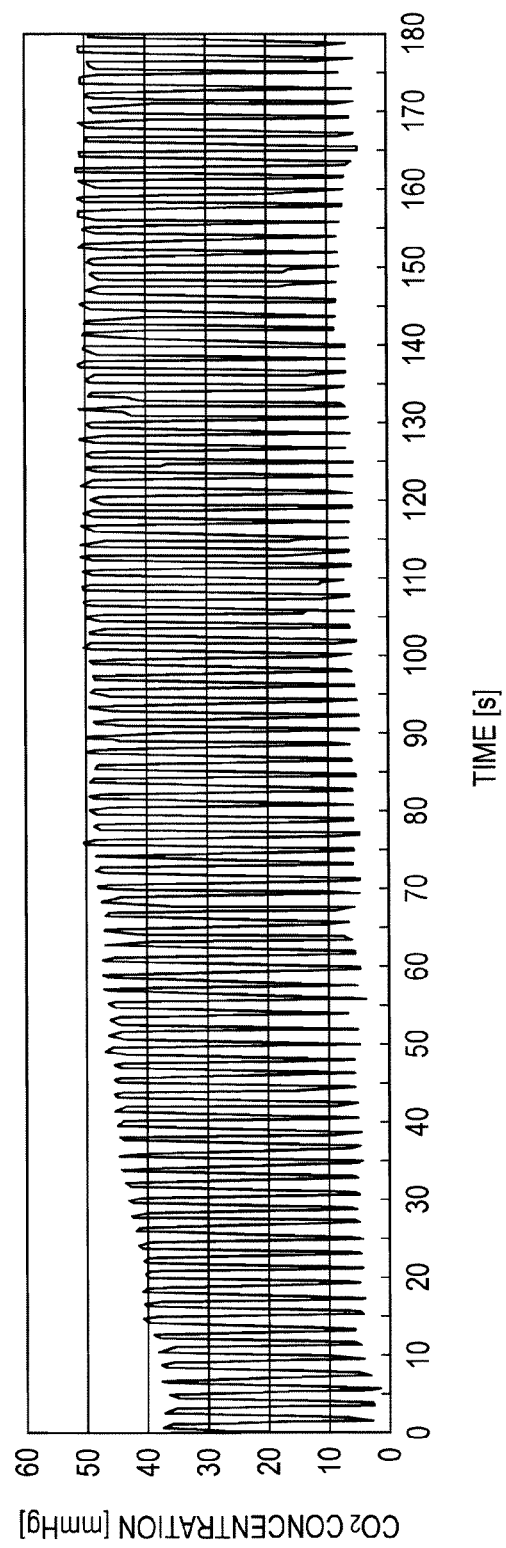
FIG. 5 is a view illustrating rebreathing in the oxygen mask of the invention.

In FIG. 5, the ordinate shows the CO2 concentration, the unit of the ordinate is mmHg, and the abscissa shows the time and indicates the CO2 concentration of each respiration of the patient. It is seen that, because of respiration, the CO2 concentration in the oxygen mask is gradually increased.

Next, the effect of reduction of rebreathing in the oxygen mask of the invention will be described with reference to FIG. 6.

Figure 6:
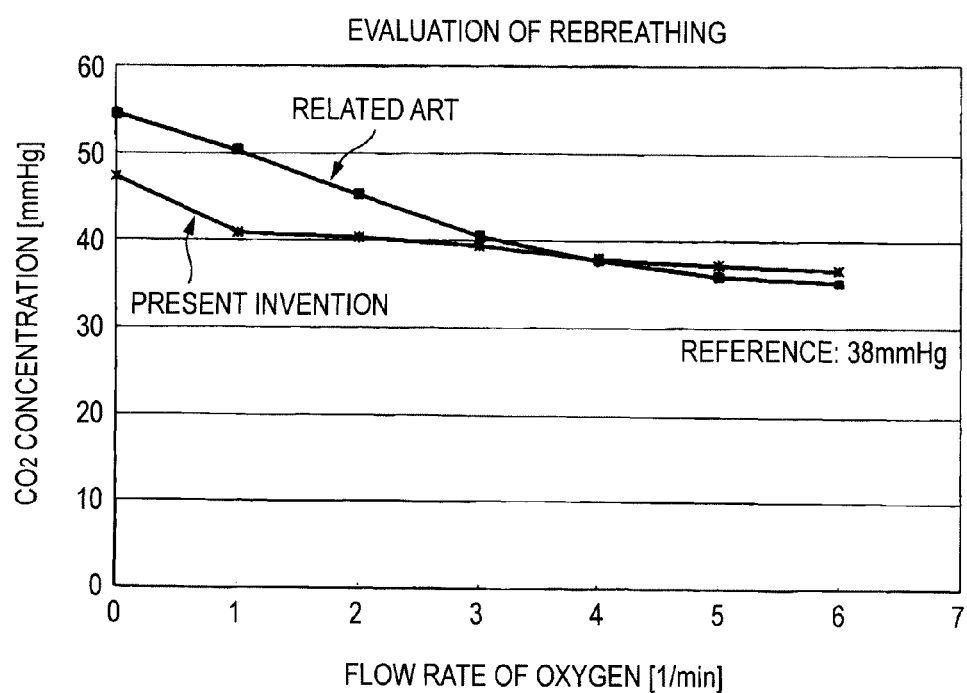
FIG. 6 is a view illustrating the effect of a countermeasure for reducing rebreathing in the oxygen mask of the invention.

In FIG. 6, the ordinate shows the CO2 concentration of the expired gas, and the abscissa shows the flow rate of oxygen supplied into the oxygen mask.

In a related-art oxygen mask, when the oxygen flow is low, expired CO2 is rebreathed, and the CO2 concentration rises.

In the oxygen mask of the invention, by contrast, the large opening is formed, and hence it is seen that the rise of the CO2 concentration due to rebreathing is reduced.

Figure 7A:
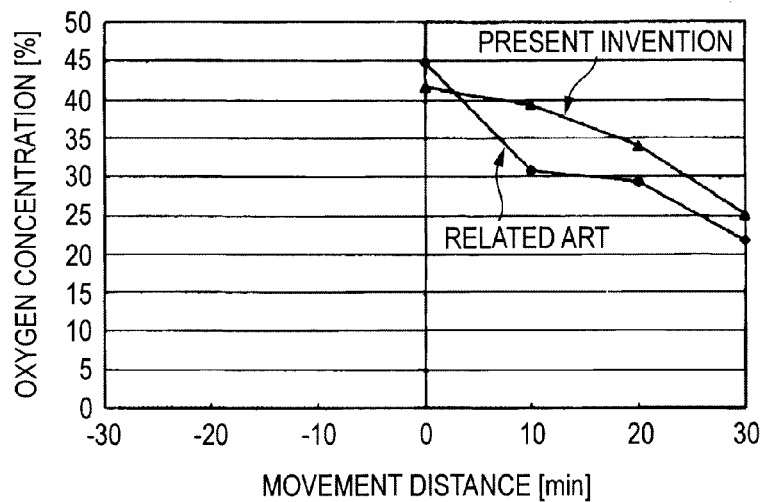
FIGS. 7A to 7C are views showing results of comparisons of the oxygen mask of the invention and a related-art oxygen mask with respect to a change of the oxygen concentration in the oxygen mask in the case where the oxygen mask is deviated from the face of the patient.
Figure 7B:
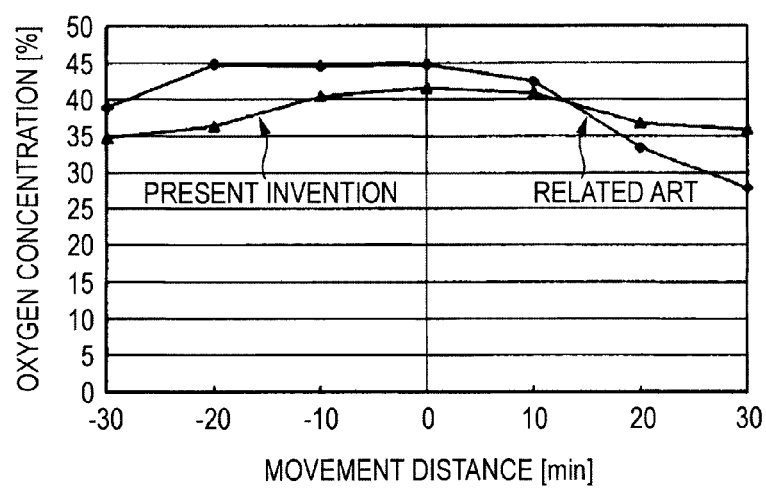
Figure 7C:
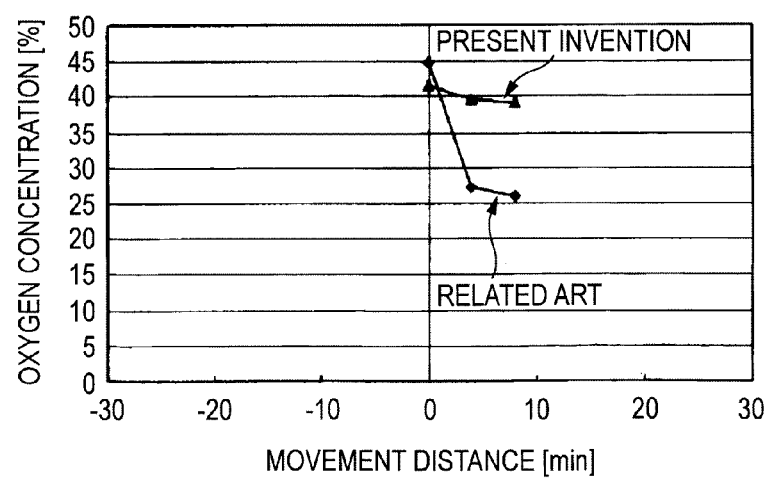
Figure 8:
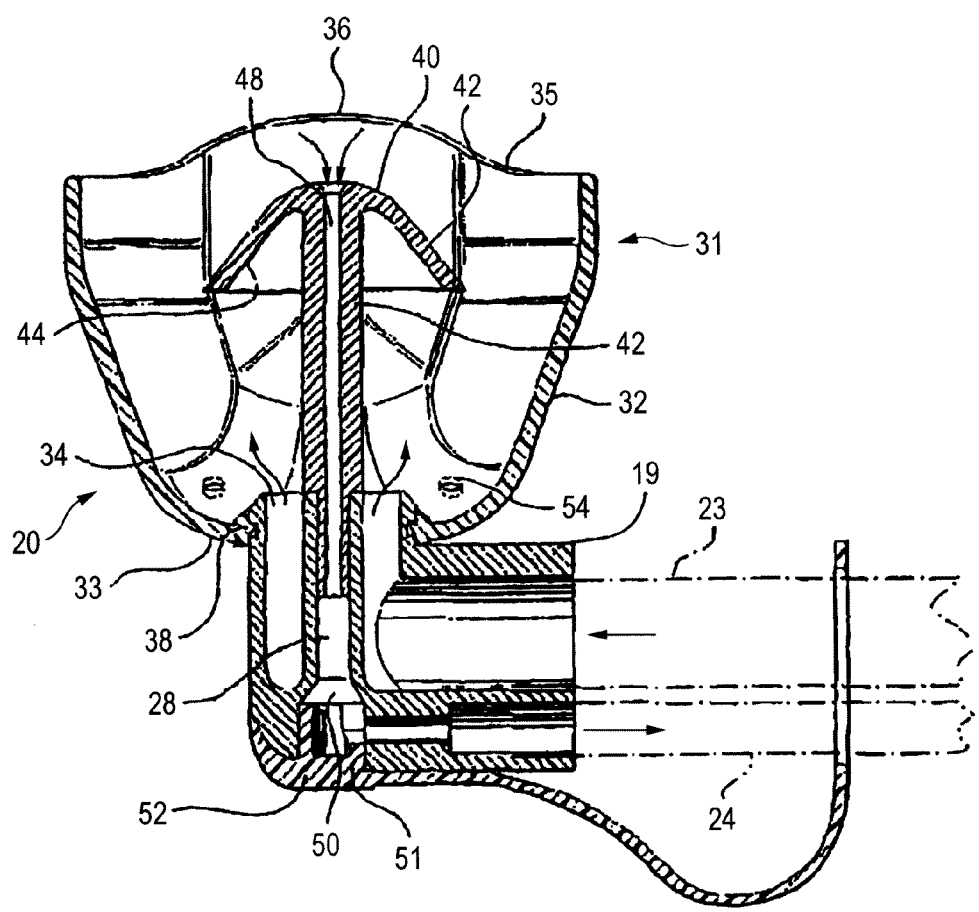
FIG. 8 is a view showing the configuration of a related-art oxygen mask in a state where an expired gas concentration measurement unit is attached to the mask.

Next, results of comparisons of the oxygen mask of the invention and the related-art oxygen mask with respect to a change of the oxygen concentration in the oxygen mask in the case where the oxygen mask is deviated from the face of the patient are shown in FIGS. 7A to 7C.

FIGS. 7A to 7C shows results of measurements in which the oxygen dosage is 6 litters/minute, the tidal volume is 140 CC/ventilation, and the respiration rate is 32 times/minute.

FIG. 7A shows results of measurements in which the oxygen concentration in the oxygen mask is measured with respect to the movement distance in the case where the oxygen mask is deviated in the lateral direction.

It is seen that, in the oxygen mask of the invention, the reduction of the oxygen concentration in the case of the lateral deviation is low as compared with the related-art oxygen mask.

FIG. 7B shows results of measurements in which the oxygen concentration in the oxygen mask is measured with respect to the movement distance in the case where the oxygen mask is deviated in the vertical direction.

Similarly, it is seen that, in the oxygen mask of the invention, the reduction of the oxygen concentration in the case of the vertical deviation is low as compared with the related-art oxygen mask.

FIG. 7C shows results of measurements in which the oxygen concentration in the oxygen mask is measured with respect to the movement distance in the case where the oxygen mask is deviated in the height direction.

Similarly, it is seen that, in the oxygen mask of the invention, the reduction of the oxygen concentration in the case of the height deviation is low as compared with the related-art oxygen mask.

From the above, it is understood that, in the oxygen mask of the invention, the effect that the change of the oxygen concentration in the oxygen mask is small irrespective of that of the attachment state with respect to the patient is obtained.

Although the preferred embodiment of the invention has been described, the invention is not limited to the above-described embodiment. For example, the oxygen mask may be configured so that oxygen scattering plates are not used, an opening is formed, and an oxygen tube is connected to a side face of the mask. In this case, the effects due to oxygen scattering plates are not obtained but the oxygen mask can have a configuration in which a medical person can more easily perform a procedure. Anyway, various design changes may be made without departing from the spirit of the invention.

According to an aspect of the invention, it is possible to realize an oxygen mask in which the degree at which the expired gas is diluted by oxygen is reduced, thereby enabling the concentration of the expired gas to be correctly measured.

What is claimed is:

1. An oxygen mask, comprising:
an oxygen supply unit for supplying oxygen to a patient; and
an attachment unit adapted to be attached to a periphery of a nose, or a nose and a mouth, of the patient including:
a first opening configured to be positioned about at least one of the nose and the mouth of the patient and having a first central axis;
a second opening which communicates with external air and which is formed at a position to which, when the oxygen mask is attached to the patient, at least one of the nose and the mouth of the patient is opposed, and has a second central axis substantially parallel or collinear with the first central axis; and
a first oxygen scattering plate which is attached to a first side of the attachment unit and extending from the first side of the attachment unit to a position opposed to an oxygen blow out port of the oxygen supply unit,
wherein oxygen blown out from the oxygen blow out port collides with the first oxygen scattering plate to prevent the oxygen from being directly blown into the patient.

2. The oxygen mask according to claim 1, wherein the attachment unit includes a second oxygen scattering plate which is attached to a second side of the attachment unit and extending from the second side of the attachment unit to a position opposed to the oxygen blow out port of the oxygen supply unit.

3. The oxygen mask according to claim 1, wherein the first oxygen scattering plate is directly attached to the first side of the attachment unit.

4. An oxygen mask comprising:
an oxygen supply unit for supplying oxygen to a patient; and
an attachment unit adapted to be attached to a periphery of a nose, or a nose and a mouth, of the patient, the attachment unit including:
a first opening configured to be positioned about at least one of the nose and the mouth of the patient and having a first central axis;
a second opening which communicates with external air, and has a second central axis substantially parallel or collinear with the first central axis of the first opening; and an oxygen scattering plate which is attached to the attachment unit and opposed to a direction in which an oxygen blow out port of the oxygen supply unit is opened,
wherein oxygen blown out from the oxygen blow out port collides with the oxygen scattering plate to prevent the oxygen from being directly blown into the patient.

5. The oxygen mask according to claim 4, wherein the oxygen scattering plate is formed by a bridging member between an attachment portion of the attachment unit and the oxygen supply unit.

6. The oxygen mask according to claim 4, wherein the oxygen scattering plate has a bent shape.

7. The oxygen mask according to claim 4, further comprising: an expired gas introduction unit into which expired gas in the oxygen mask is introduced; and an expired gas concentration measurement unit being attachable to and detachable from an outer side of the expired gas introduction unit.

8. The oxygen mask according to claim 7, wherein the expired gas concentration measurement unit is movably attached to the expired gas introduction unit.

9. The oxygen mask according to claim 7, further comprising an adjusting unit which adjusts an attaching position of the expired gas introduction unit.

10. The oxygen mask according to claim 7, wherein the expired gas introduction unit includes a rebreathing prevention hole for preventing rebreathing of expired gas from occurring.

11. The oxygen mask according to claim 4, further comprising: an expired gas introduction unit into which expired gas in the oxygen mask is introduced; and a sampling tube is attachable to and detachable from an outer side of the expired gas introduction unit.

12. The oxygen mask according to claim 11, wherein the sampling tube is movably attached to the expired gas introduction unit.

13. The oxygen mask according to claim 11, wherein the expired gas introduction unit includes a rebreathing prevention hole for preventing rebreathing of expired gas from occurring.

14. The oxygen mask according to claim 4, wherein a portion of the oxygen mask which is to be in contact with the patient is inwardly curled.

15. The oxygen mask according to claim 4, wherein an insertion port of a stomach tube is formed in a portion of the oxygen mask which is to be in contact with the patient.

16. The oxygen mask according to claim 4, wherein an oxygen supplying tube is connected to the oxygen supply unit from a side face of the oxygen mask.

17. The oxygen mask according to claim 4, wherein the oxygen scattering plate is directly attached to a first side of the attachment unit.

18. An oxygen mask, comprising:
an oxygen supply unit for supplying oxygen to a patient;
an attachment unit including a first opening having a first central axis and adapted to be attached to a periphery of a nose, or a nose and a mouth, of the patient, the attachment unit including a second opening having a second central axis substantially parallel or collinear with the first central axis of the first opening, the second opening communicating with external air, the attachment unit including an oxygen scattering plate which is attached to a side of the attachment unit and extending from the side of the attachment unit to a position opposed to an oxygen blow out port of the oxygen supply unit;
a first oxygen supplying tube connected to the oxygen supply unit from a first side face of the oxygen mask; and
a second oxygen supplying tube connected to the oxygen supply unit from a second side face of the oxygen mask,
wherein oxygen blown out from the oxygen blow out port collides with the oxygen scattering plate to prevent the oxygen from being directly blown into the patient.

19. The oxygen mask according to claim 18, further comprising: an expired gas introduction unit into which expired gas in the oxygen mask is introduced; and an expired gas concentration measurement unit being attachable to and detachable from an outer side of the expired gas introduction unit.

20. The oxygen mask according to claim 19, wherein the expired gas introduction unit includes a rebreathing prevention hole for preventing rebreathing of expired gas from occurring.

21. The oxygen mask according to claim 18, further comprising: an expired gas introduction unit into which expired gas in the oxygen mask is introduced; and a sampling tube is attachable to and detachable from an outer side of the expired gas introduction unit.

22. The oxygen mask according to claim 21, wherein the expired gas introduction unit includes a rebreathing prevention hole for preventing rebreathing of expired gas from occurring.

23. The oxygen mask according to claim 18, wherein a portion of the oxygen mask which is to be in contact with the patient is inwardly curled.

* * * * *